United States Patent [19]
Gamberini

[11] Patent Number: 5,814,346
[45] Date of Patent: Sep. 29, 1998

[54] COMPOUND FOR TREATING ANIMAL EXCREMENT

[75] Inventor: Bruno Gamberini, Via Pier de Crescenzi, Italy

[73] Assignee: Progetto Emme S.r.l., Bologna, Italy

[21] Appl. No.: 659,432

[22] Filed: Jun. 6, 1996

[30] Foreign Application Priority Data

Jun. 9, 1995 [IT] Italy ................................ BO95A0293

[51] Int. Cl.⁶ .......................... A01N 59/02; A01N 59/06; A61L 11/00; A61L 2/16
[52] U.S. Cl. .......................... 424/665; 424/600; 424/661; 424/682; 424/688; 424/693; 424/694; 424/703; 424/705; 424/724; 424/76.6; 424/76.8; 424/405; 424/406; 424/409; 424/489; 119/171; 119/173; 422/5; 422/28; 422/37; 514/951
[58] Field of Search ..................................... 424/600, 661, 424/682, 688, 693, 694, 703, 705, 76.6, 76.8, 405, 406, 409, 489, 665, 724

[56] References Cited

U.S. PATENT DOCUMENTS

| | | | |
|---|---|---|---|
| 4,607,594 | 8/1986 | Thacker | 119/172 |
| 5,154,594 | 10/1992 | Gamlen | 119/171 |
| 5,450,817 | 9/1995 | Hahn et al. | 119/173 |

FOREIGN PATENT DOCUMENTS

| | | |
|---|---|---|
| 2169484 | 7/1986 | United Kingdom . |
| 8102891 | 10/1981 | WIPO . |
| 9325329 | 12/1993 | WIPO . |

OTHER PUBLICATIONS

Chemical Abstracts 106:69577, 1987.

EPO Search Report, Jun. 1997.

*Primary Examiner*—John Pak
*Attorney, Agent, or Firm*—Hall, Priddy & Myers

[57] ABSTRACT

The compound, in use, is sprinkled over the excrement for treatment to neutralize and eliminate the odour, spores, fungi, bacteria and microorganisms therein, and presents a first subcompound in powder comprising a mixture of diatoms (often referred to as infusorial earth), a calcium-based substance and a sulphur-based substance.

4 Claims, No Drawings

COMPOUND FOR TREATING ANIMAL EXCREMENT

BACKGROUND OF THE INVENTION

The present invention relates to a compound for treating animal, particularly dog, excrement.

As is known, a major problem in towns, very often due to bad manners on the part of the inhabitants, is the accumulation of dirt and refuse of all kinds, particularly dog excrement, which often makes pavements and parks unwalkable, and, moreover, is a source of odour, spores, fungi, bacteria and microorganisms.

SUMMARY OF THE INVENTION

It is an object of the present invention to provide a chemical compound for neutralizing the odour, spores, fungi, bacteria and microorganisms present in animal excrement.

Further objects and advantages of the present invention will be disclosed in the following description.

According to the present invention, there is provided a compound for treating animal excrement, and which, in use, is sprinkled onto the excrement for treatment to neutralize and eliminate odour, spores, fungi, bacteria and microorganisms therein; the compound being characterized by presenting a first subcompound of powder comprising a mixture of diatoms (often referred to as infusorial earth), a calcium-based substance and a sulphur-based substance.

A preferred, non-limiting embodiment of the present invention will now be described by way of example.

DETAILED DESCRIPTION OF THE INVENTION

The present invention relates to a chemical compound for treating animal, in particular dog, excrement. The compound is in the form of powder, and, in use, is sprinkled onto the excrement for treatment to neutralize and eliminate odour, spores, fungi, bacteria and microorganisms therein. As is known, animal excrement substantially comprises water, digestive residue, spores, fungi, bacteria and microorganisms.

The chemical compound according to the present invention comprises a mixture of two subcompounds: a first comprising diatoms (often referred to as infusorial earth), a calcium-based substance and a sulphur-based substance; and a second comprising one or a mixture of the following products: sand, wood flour (sawdust) and cement mix. The first subcompound constitutes 10–30%, and preferably 20%, of the compound.

Diatoms constitute 6–18%, and preferably 12%, of the compound. As is known, diatoms are a natural form of volcanic siliceous rock, which contains 2–5% of combined moisture enabling it to expand up to 20 times its original volume if subjected to thermal shock. When so expanded, this mineral gives rise to an infinite number of different forms of granules, which, if ground and sized, constitute a filtering material of an exceptional specific surface. The high degree of porosity at 85% of the volume of the diatom comprises minute interconnected pores or vacuoles; the high absorption capacity of the diatom enables it to absorb liquids up to one and a half times its own weight while still maintaining the properties of a dry powder; and the particle structure, large surface area and irregular shape of the diatom constitute an extremely large specific surface area. In other words, if sprinkled onto animal excrement, diatoms absorb odour and humidity, and are receptors of microorganisms. Finally, a further point to note is that diatoms are waste products.

The calcium-based substance comprises a mixture of calcium hypochlorite $CaCl_2O_2$ and one or more of the following products: lime $CaO$, soda lime $CaO+NaOH$, hydrated lime $Ca(OH)_2$; and calcium hypochlorite constitutes 1–3%, and preferably 2%, of the compound. The product defined by one or a mixture of lime, soda lime and hydrated lime constitutes 2.5–7.5%, and preferably 5%, of the compound. Calcium hypochlorite provides for inhibiting bacteria, spores, fungi and microorganisms present in animal excrement; and the product defined by one or a mixture of lime, soda lime and hydrated lime provides for preventing the diffusion of bacterial microorganisms.

The sulphur-based substance preferably comprises a 99% concentration of flowers of sulphur, constitutes 0.5–1.5%, and preferably 1%, of the compound, and acts as a fungicide and antiseptic.

The second subcompound is for preventing slippage.

When sprinkled onto animal excrement, the compound according to the present invention provides, after a given length of time and particularly by absorbing the humidity in the excrement, for so hardening it that it may be swept away using an ordinary brush on which absolutely no traces of excrement are left, or may be vacuumed using an ordinary vacuum cleaner.

The advantages of the present invention will be clear from the foregoing description.

In particular, the present invention provides for a compound in the form of antiseptic, disinfectant powder, which, on the one hand, eliminates the odour and the spores, bacteria, fungi and microorganisms which reproduce in animal excrement, and, on the other, hardens the excrement to enable it to be removed and disposed of as solid refuse. Such a compound is particularly useful for treating dog excrement with which the pavements and parks in towns are increasingly littered, thus affording advantages not only in terms of hygiene (especially as regards children) but also in terms of neatness. Moreover, the compound according to the invention is nontoxic and therefore completely safe to handle in the percentages described above, and may be produced in single- or multiple-dose pocket sachets for use by dog owners as required.

Clearly, changes may be made to the compound as described herein without, however, departing from the scope of the present invention.

I claim:

1. An antiseptic powder for hardening, deodorizing, and disinfecting animal excrement comprising in admixture, an effective amount of:

a) infusorial earth;

b) calcium hypochlorite;

c) flowers of sulphur; and d) a member selected from the group consisting of lime $CaO$, soda lime $CaO+NaOH$, hydrated lime $Ca(OH)_2$ and mixtures thereof.

2. An antiseptic powder according to claim 1 wherein said admixture further includes a member selected from the group consisting of sand, wood flour, and cement mix.

3. A method of hardening, deodorizing, and disinfecting animal excrement comprising applying to said excrement an effective amount of a powder comprising an admixture of:

a) infusorial earth;

b) calcium hypochlorite;

c) flowers of sulphur; and d) a member selected from the group consisting of lime CaO, soda lime CaO+NaOH, hydrated lime $Ca(OH)_2$ and mixtures thereof.

4. A method according to claim 3 wherein said admixture further includes a member selected from the group consisting of sand, wood flour, and cement mix.

* * * * *